United States Patent
Leitinger et al.

(10) Patent No.: US 7,418,874 B2
(45) Date of Patent: Sep. 2, 2008

(54) METHOD FOR QUALITY ASSURANCE OF LONG TIMBER

(75) Inventors: Hans-Peter Leitinger, Wernersdorf (AT); Sebastian Leitinger, Wernersdorf (AT)

(73) Assignee: Holzindustrie Leitinger Gesellschaft m.b.H., Wernersdorf (AT)

(*) Notice: Subject to any disclaimer, the term of this patent is extended or adjusted under 35 U.S.C. 154(b) by 147 days.

(21) Appl. No.: 11/406,368

(22) Filed: Apr. 19, 2006

(65) Prior Publication Data

US 2006/0259252 A1 Nov. 16, 2006

Related U.S. Application Data

(63) Continuation of application No. PCT/AT2004/000362, filed on Oct. 21, 2004.

(30) Foreign Application Priority Data

| Oct. 27, 2003 | (AT) | ............................. A 1699/2003 |
| Jun. 22, 2004 | (AT) | ............................. A 1054/2004 |
| Jun. 22, 2004 | (AT) | ............................. A 1055/2004 |

(51) Int. Cl.
*G01N 3/08* (2006.01)
*G01L 1/24* (2006.01)

(52) U.S. Cl. ....................................... 73/826
(58) Field of Classification Search ............... 73/826, 73/800

See application file for complete search history.

(56) References Cited

U.S. PATENT DOCUMENTS

| 3,919,884 | A | | 11/1975 | Gunderson et al. |
| 4,321,834 | A | * | 3/1982 | Oliver .......................... 73/812 |
| 4,570,913 | A | * | 2/1986 | Rosser ......................... 269/22 |
| 4,941,357 | A | * | 7/1990 | Schajer ........................ 73/600 |
| 5,237,870 | A | * | 8/1993 | Fry et al. ...................... 73/588 |
| 5,585,732 | A | * | 12/1996 | Steele et al. ................ 324/663 |
| 5,679,190 | A | * | 10/1997 | Robinson ..................... 156/64 |
| 6,122,877 | A | * | 9/2000 | Hendrickson et al. ......... 52/520 |
| 6,231,947 | B1 | * | 5/2001 | Hill ............................. 428/120 |

FOREIGN PATENT DOCUMENTS

| DE | 76 08 950 | 9/1976 |
| DE | 34 12 675 | 10/1985 |
| DE | 40 12 444 | 10/1991 |
| DE | 41 40 349 | 10/1992 |
| DE | 20 2004 001 914 | 5/2004 |
| EP | 0 380 057 | 8/1990 |

* cited by examiner

*Primary Examiner*—Max Noori
(74) *Attorney, Agent, or Firm*—Dickstein Shapiro LLP (57) ABSTRACT

The invention relates to a method for quality assurance in preferably finger-jointed timber (1), produced in series, with a given minimum length (12), characterized in that each piece, produced within the length (12), is loaded with increasing tensile forces at the ends (5) thereof to a threshold value, below the breaking load for a fault-free timber piece, and the length changes (DELTA 1), changing therewith, are determined over a section, or the whole length of the timber piece (1) and used as a quality criterion for the use, or the further processing of the timber piece (1). The invention further relates to a device for carrying out said method.

27 Claims, 8 Drawing Sheets

METHOD FOR QUALITY ASSURANCE OF LONG TIMBER

This is a continuation of International Application No. PCT/AT2004/000362, filed on Oct. 21, 2004.

BACKGROUND OF THE INVENTION

1. Field of the Invention

The invention relates to a method for quality assurance of preferably finger-jointed long timber, produced in series and having a predetermined minimum length, in particular of structural solid wood, as well as to a device for carrying out the method.

2. Description of the Related Art

In order to manufacture from tree trunks a high-quality long timber as used, for instance, as structural timber, thereby ensuring a reasonably uniform quality, the tree trunks are cut or formatted, respectively, to the desired dimension, and, if the blanks thus broken down exhibit defective spots also known as weak points such as loose branches etc., those defective spots or weak points, respectively, are removed and the remaining blank pieces are glued together to form a long timber by means of finger joints on the front side. In this way, glue-laminated timber is produced which is formed from several layers of longitudinally jointed boards glued together and exhibiting finger joints in an offset manner. Laminated squared timber is manufactured from two to three beams glued together longitudinally, which optionally are likewise comprised of sections connected by finger jointings.

A specific problem arises with regard to the processing of strong timber, meaning trees which, at breast height, have a diameter of more than approx. 50 cm. If such strong timber is processed into structural solid wood, it has the advantage of a higher yield. However, the timber properties are very heterogeneous, i.e., the strong timber involves higher selection efforts. In addition, a wet core or a heart shake may cause problems. Strong branches likewise cause poorer mechanical properties. For this reason, long timber manufactured from strong timber can only rarely be cut from a tree trunk in one piece; mostly, it is necessary to cut out weak points and to glue the sections together by finger jointing, as mentioned above, in order to form a long timber.

It is known to carry out this process in a more or less automated fashion, with the wood first passing through a quality sorting plant in which it is examined for moisture, tree-ring density, quality of colour and texture, branches etc., which can either be done visually or by electric resistance measurement (for humidity measurement) or using laser cameras. X-ray or computer-tomography or ultrasonic technology is used for detecting hidden branches. Cutting out the defective spots and sticking together the finger jointing is usually performed in automatically controlled installations.

In order to assure the quality of finger jointings manufactured in such installations, destruction tests are carried out, wherein, in a bend test provided for such a destruction test, no breakage is allowed to occur in the region of the finger jointing.

It has been shown that, if long timber manufactured in this manner is used, unexpected breaks—caused, for example, by compressive breaks e.g. in wind fallen wood, gluing errors, tooth forming errors, internal cracks etc.—may occur despite automated error detecting methods and despite a subsequent intensive visual inspection so that there are attempts to exclude structural solid wood from wooden constructions in which timber has a supporting function. This is disadvantageous especially since, due to this, an inexpensive utilization as a squared timber made of strong timber would no longer be possible, i.e., the strong timber would also have to be processed into multilayered glue-laminated timber or laminated squared timber, wherein hidden or undetected defective spots or weak points, respectively, in individual sections are of less consequence as a result of multilayered gluing.

SUMMARY OF THE INVENTION

It is the object of the invention to provide a method for quality assurance of long timber produced in series, no matter if shaped in the form of glue-laminated timber or laminated squared timber or structural solid wood, laminated chip wood, laminated veneer wood, in order to be able to efficiently use such kind of long timber also for structural parts which are subject to higher stress. In particular, it should be possible to strongly reduce the cross-section surcharges which presently are required due to the timber's inhomogeneity.

Since strong timber is predominant in forests and the amount of strong timber is still increasing, a specific object of the invention is to be able to use just this strong timber also with the required safety for highly stressed structures in which long timber assumes supporting functions, wherein the long timber is shaped as a structural solid wood, i.e., is not formed from individual timber layers glued together longitudinally.

According to the invention, said object is achieved in that each long timber finished within the length, preferably each long timber completely glued together, is loaded with tensile forces engaging the respective ends thereof and increasing to a threshold value below the breaking load of a faultless long timber, and the change in length increasing therewith is determined in at least one section or across the entire length of the long timber and is used as a quality criterion for the use, or the further processing, respectively, of the long timber.

The invention is based on the realization that, in a tensile test for timber, no deterioration of timber properties occurs below the breaking limit due to the strict linearity between the change in length and the tension.

Thereby, in order to determine the change in length, the laser speckle method or a method of differential length measurement is preferably used with a direct measuring method or indirect measuring methods such as, e.g., a resistance change in strain gauges.

If the long timber breaks in the tensile test, the tensile stress determined during the breakage is preferably used for classifying the quality of the broken pieces for further usage or subsequent processing thereof.

A preferred variant is characterized in that, in case an inadmissibly high change in the length of the long timber is determined at a predetermined tensile force, the long timber is eliminated from the production, the weak point of the long timber causing the inadmissible change in length or the weak points of the long timber, respectively, is/are cut out and the remaining parts of the long timber that are free from weak points are assembled by finger jointing into a new long timber, optionally with further long timber parts being added, whereupon the newly produced long timber is again subjected to the method according to claim 1.

Making use of the above-indicated realization, a tension test can be performed in the production process up to the breaking limit (test for determining the breaking limit). The test report shows the stress at break. If the point of break is removed by lopping after the breakage and the broken pieces are possibly reconnected, for example, by finger jointing, no repeated breakage can occur in a repeat of the tension test up to, at most, the breaking limit (if jointing is correct), since all the other points of the timber have already passed the test without problems. In order to maintain the full material length, a new part of high quality can be inserted after removal of the broken section. In doing so, however, a higher risk of repeated breakage occurs (two jointing points, untested new material). Suitably, the second tension test is carried out with a strongly reduced tensile load but with a loading that is sufficient for the desired strength requirement. With broken pieces having a sufficient size for further processing, the material thus obtained can directly be regarded as thoroughly tested after the broken ends have been lopped off, and a second tensile test can be omitted.

By these measures, it is possible to successfully reintroduce the long timber eliminated during the tensile test into the production process so that an optimum utilization of timber will be provided, with the amount of waste and/or cuttings being as small as possible.

Suitably, the tensile forces are applied to the long timber via clamping jaws provided at the ends of the long timber on two opposing sides.

Advantageously, each tested long timber is provided with a quality mark.

Finish-machining of the long timber such as, for example, by planing, grinding or milling is preferably carried out after the test.

It has turned out to be advantageous that the long timbers are allocated to at least two different quality classes depending on the result of the length change determination, whereby it is possible to provide the product which is most suitable for each specific requirement in terms of strength values and to efficiently use also long timber which does not meet the highest demands.

After a surface analysis, the raw material, being undivided and/or divided into sections, is preferably sorted into quality classes and is subjected in each quality class as an individual long timber to a method for quality assurance according to claim 1, optionally after finger jointing.

It is a further object of the invention to provide a method by means of which beams and binders, respectively, for wooden constructions made of quality-assured long timber can be manufactured, which beams and binders have very large cross-sections and can thereby fully assume a supporting function which is at least equivalent to that of a glue binder made of glue-laminated timber, and preferably have an even higher load-bearing capacity.

According to the invention, said specific object is achieved in that at least two long timbers tested in accordance with claim 1, which meet a quality criterion required for an application, are glued together, whereby a beam having an upright glued joint is formed.

In doing so, it is essential that the long timbers were subjected to a quality assurance test according to claim 1, i.e., have been tested across their entire length, before they are formed into a beam. Thereby, it is possible to use strong timber—with the quality being at least the same as with beams formed, e.g., from boards in a conventional manner.

Particularly good adhesion and gluing, respectively, of the long timbers for forming a beam is ensured if the vertical side faces of the long timbers, which side faces are glued together, are processed by milling prior to gluing.

Depending on the required load-bearing capacity of a beam, three or more long timbers arranged side by side can also be glued together to form a beam.

In order to form a binder from the beams manufactured according to the invention, beams which in each case have an upright glued joint are preferably placed on top of each other and glued together to form a beam binder.

A beam manufactured according to the method of the invention is characterized in that it exhibits at least one upright glued joint and that the side faces forming the glued joint are preferably processed by milling.

A beam binder is suitably formed by two or more beams arranged on top of each other and glued together.

According to the invention, a specific optical advantage is provided for the wooden architecture, particularly since the vertical side faces of a beam or of a beam binder exhibit a speckled texture rather than showing, as with a glue-laminated timber, only narrow boards glued together and comprising the glued joints.

Preferably, a beam or a beam binder, respectively, is characterized in that it is formed from long timbers having a height of more than 100 mm, preferably of up to about 300 mm, and a width of more than 50 mm, preferably of up to 100 mm.

In order to be able to use extra high strength zones of the sapwood area of a tree trunk in the high-stress area of a carrier, a beam or a beam binder, respectively, is characterized according to a preferred embodiment in that it is formed from long timbers having a height of more than 300 mm, preferably of up to 600 mm, and a width of more than 50 mm, wherein long timbers are used the narrow edge regions of which are cut from the sapwood of a strong timber.

In order to ensure a speckled texture also at the bottom side and/or the top side of a beam or beam binder, respectively, a beam or a beam binder is suitably characterized by the arrangement and gluing of at least one long timber at the bottom side and/or top side, which long timber extends across the entire width of the beam or beam binder, respectively, and is likewise tested and exhibits a speckled texture towards the bottom or the top, respectively.

A device for carrying out the test is characterized by a tension testing facility applying tensile forces to a long timber and comprising clamping jaws whose sides engaging the long timber are provided with grooves having an arcuate, preferably circular-arc-shaped, cross-section and running transversely to the direction of loading.

For better power transmission, adjacent grooves have different depths, with adjacent grooves suitably exhibiting cross-sections having different curvatures as well as different widths.

In order to avoid that the long timber to be tested is damaged by the clamping jaws, said clamping jaws are characterized according to a preferred embodiment in that a groove having a larger depth and width and a less pronounced curvature is in each case followed by a groove having a smaller depth and width and a more pronounced curvature, with the grooves advantageously being arranged next to each other.

Furthermore, it is an object of the invention to provide a tension testing device for timber for testing timber pieces produced in series, in particular long timber, no matter if shaped in the form of glue-laminated timber or laminated squared timber or structural solid wood, laminated chip wood, laminated veneer wood, in order to be able to efficiently use such kind of long timber also for structural parts which are subject to higher stress. In particular, it should be possible to strongly reduce the cross-section surcharges which presently are required due to the timber's inhomogeneity.

Since strong timber is predominant in forests and the amount of strong timber is still increasing, a specific object of the invention is to provide a timber tension testing device for said strong timber, wherein the long timber is shaped as a structural solid wood, i.e., is not formed from individual timber layers glued together longitudinally.

According to the invention, said object is achieved by combining the following features:
- a test bed, in particular an engine bed, having a length corresponding to the maximum length of the timber piece to be tested,
- a first tensioning trestle arranged, preferably fixedly arranged, in an end region of the test bed,
- a second tensioning trestle movable along the test bed and adjustable to the length of the timber piece to be tested,
- clamping jaws provided at both tensioning trestles which grip and clamp a timber piece brought into the test position from above and from below,
- a device for the application of force onto a clamped timber piece by means of a tensioning trestle,
- a cross conveyor for conveying a timber piece from a buffer zone for timber pieces, which is arranged at the side of the test bed, to the test bed and onwards to a storage zone arranged opposite the buffer zone and at the side of the test bed and receiving the tested timber pieces, as well as
- a centering means for centering a timber piece brought into the test position between the clamping jaws.

In this way, it is possible to test each timber piece as a whole and provide it for a specific use depending on the respective test result, without any risk of breakage as it always exists, for example, in strong timber as presently used.

Thereby, the cross conveyor is preferably formed by several conveyor chains arranged side by side.

According to a preferred embodiment, the centering means comprises two centering arms which are movable, preferably pivotable, from a rest position above the upper clamping jaw into a centering position disposed beside the clamping jaws, wherein the centering arms are advantageously movable synchronously against the timber piece, namely in each case from one side.

A particularly simple device for carrying out a length difference measurement is characterized in that a scanner to be applied to a front surface of a timber piece is provided on each tensioning trestle.

BRIEF DESCRIPTION OF THE DRAWINGS

Below, the invention is illustrated in further detail by way of the drawing, with FIG. 1 showing a block diagram of the process steps of the manufacturing process according to the invention and FIG. 2 showing a typical tensile stress curve for a finger-jointed long timber.

FIG. 16 concerns a side view and

DETAILED DESCRIPTION OF THE PREFERRED EMBODIMENT

The timber prepared by natural (open air drying) or technical drying (e.g. in electronically controlled drying chambers) so as to reach a predetermined value such as, e.g., 15%±3% residual moisture is supplied to a solid wood processing plant by means of stackers or other conveying means. Rough wood products having a specified length (e.g. 4 m or also significantly more) and a particular cross-section dimensioning (particular cut dimensions) as well as qualities as comparable as possible usually serve as starting products for a standard squared-timber product.

At first, each piece of said greenware is tested for its moisture content. This is done most precisely by the kiln-drying test, in doing so, the weight loss of a test piece is determined during selective drying in a kiln. The electric resistance measurement (conductivity measurement) by means of probes (ram electrodes) penetrating deeply into the timber at two or more defined points is more practicable. However, capacitive methods (megahertz region) can also be used for a contactless humidity measurement, with the specific inductive capacity depending on the water density in the timber. Infrared measuring methods, chemical measuring methods (e.g. indicator paper), neutron scattering methods can be applied. Microwave measuring methods are also possible for the determination of moisture. Stray field sensors, radiation field sensors or resonators can also be used for the determination of moisture. Besides, there is the possibility to determine the moisture in a drill hole via hygrometers.

The first selection stage consists in moisture testing. Raw material that is too wet is again subjected to drying.

A short first cut at the front surface serves for neatly exposing the cross-sectional structure in order to measure the density of tree rings. The measurement is effected visually by cameras, laser focussing and image processing software or other measuring means. This second stage of selection enables the automatic and computer-assisted classification of tree trunks into various quality classes based on tree-ring widths. The higher the density of the rings and the smaller the distances between tree rings, the higher are the strength and hence the quality. Branches have a strength reducing property, since the tree-ring formation involves imperfections.

A surface analysis with regard to colourings, frequency of branches, cracks and other quality characteristics detectable by camera and electronic image data processing is performed in parallel. The timber elements thus detected and suitable in terms of quality are subsequently cut with saws to the crude cross-section, unless they are thitherto already provided as suitable scattered squared-timber rods exhibiting the irregularities in shape caused by shrinkage on drying. Each scattered rough wood is rough-planed on at least two sides in order to obtain clearly defined reference surfaces for further processing for the jointing technique.

In order to determine the inner timber quality, each timber is subjected to an echo depth sounding test either with X-rays in one or several directions or by computer-tomography technology via ultrasound. The results are processed in a computer-assisted fashion using calculators, computers or processors and are stored for further processing of the timber. Here, all defective spots are detected, for the subsequent lopping, in an automated fashion but also via an additional visual inspection by trained personnel, and the data such as lopping positions, quality levels are used for further control of the machine.

Suitable sections having minimum lengths which result from the limitations brought about by the plant are cut with the lopping saw from the preselected timbers. In case of sufficient suitability, the raw material is subjected to further processing also in an undivided state. Based on the data ascertained from the main selection, the pieces thus formed are sorted into various quality classes and are supplied separately via conveyors to one or several jointing plant(s) such as (a) finger-jointing plant(s).

Normally, the sections are provided with dovetails on the front side using a milling cutter, are glued and pressed together and taken via conveyors to the storage for glue aging, where they will again rest separately according to the quality levels corresponding to the main sorting until the glued joint exhibits the required strength. Alternatively, other jointing techniques can also be used. Long timbers resulting therefrom are stored in different quality classes in a logistically separated way. Each quality level has its specific characteristics such as appearance and strength class. The number of quality classes can be defined arbitrarily.

To provide a simpler explanation, three quality levels will be looked at. Quality A of high grade, strength and suitability for the visible range (e.g. standard class S 13), Quality B with suitability for the invisible range (e.g. standard class S 10) and quality R with visible cracks due to the shrinkage caused by drying. Depending on the respective class and timber dimension, various maximum allowable tensile stress loads occur in a further tensile test.

The long timbers which are finger-jointed or connected otherwise are taken to the final testing via cross and longitudinal conveyors prior to or after planing and chamfering. In doing so, each individual long timber is clamped into the tension testing plant by clamping means, the tensile load is then increased to the preadjusted test load (depending on the cross-section and the quality class) and the change in length is recorded via measuring means (e.g. according to laser speckle). For example, the modulus of elasticity is calculated therefrom. In case of breakage or moduli of elasticity which no longer follow Hooke's law, the test procedure is terminated, the defective spot or weak point, respectively, (e.g. bad finger jointings) is located and removed and the resulting timber pieces are reintroduced into the production cycle and allocated as sections of an inferior or equal quality level. Beforehand, a splitting of the rods or broken pieces might be necessary. In case of inadmissible moduli of elasticity or an excessive change in length, respectively, the timber thus tested is either likewise returned to the working cycle, whereby further presumed weak points are split and lopped off, or the timber is checked for lower quality criteria and allocated to them. If the timber breaks, it always breaks at its weakest point. The point of break is removed (lopped off) when the defective timber is returned to the production process. Thereby, the quality of a long timber produced cyclically in this manner is, in principle, increased from cycle to cycle, using a jointing technology such as finger jointings. In order to avoid damage to plant facilities and for accident prevention, protective means such as protecting caps can be disposed around the test section, which in case of breakage (failure) of the test sample catch parts that are splintering off. Nevertheless, a greater yield can be obtained from the rough wood, in particular strong timber, via this method.

If the product passes the tensile test, it is provided with the test results. This can be done after planing and chamfering directly on the product by embossing, imprinting with coded or uncoded measured values and other data such as manufacturing date, quality class, firm name and the like, or separately on protocols which are applied or added to the subsequent package either with stickers or directly.

Figure 1:
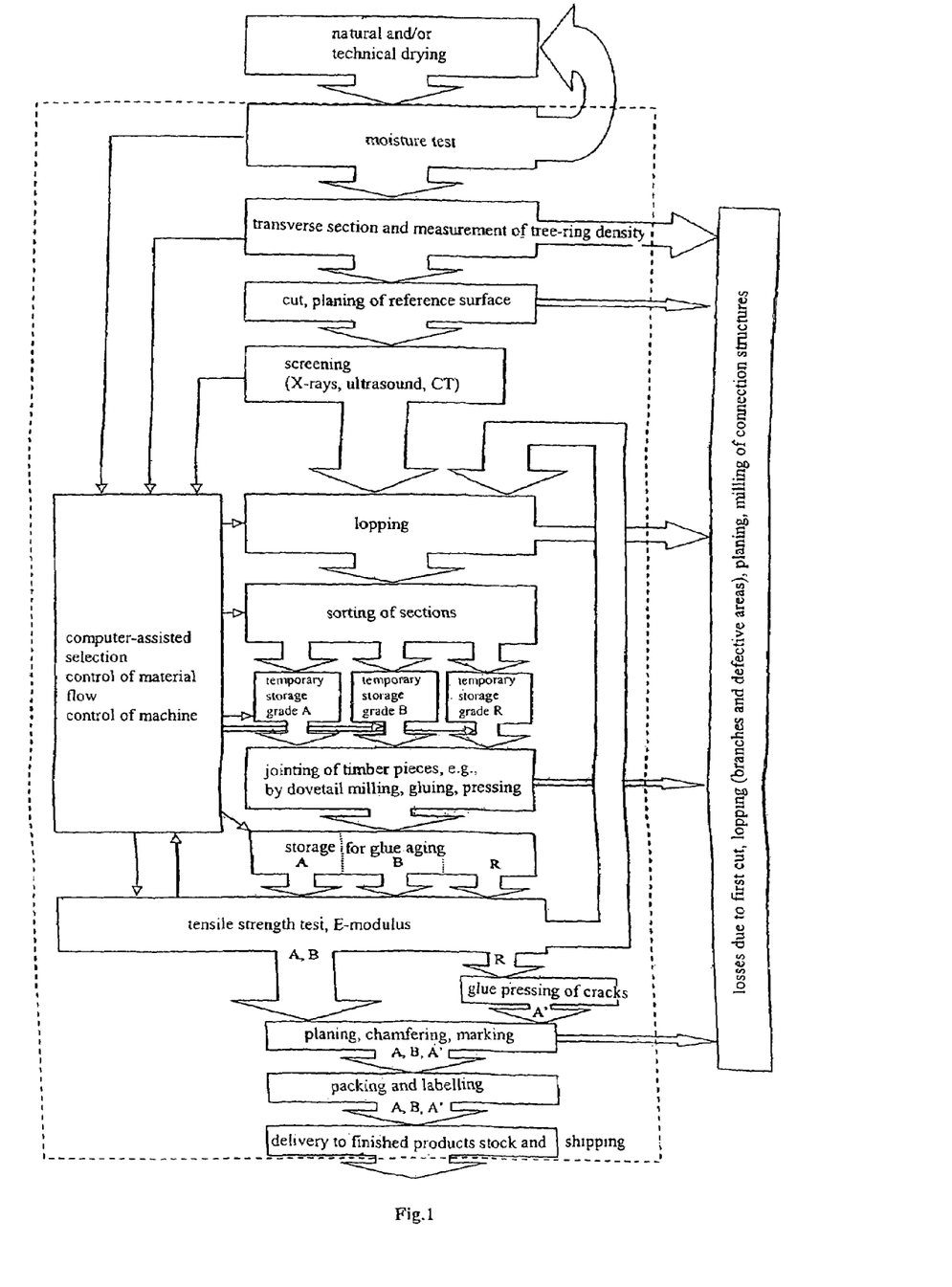
Figure 2:
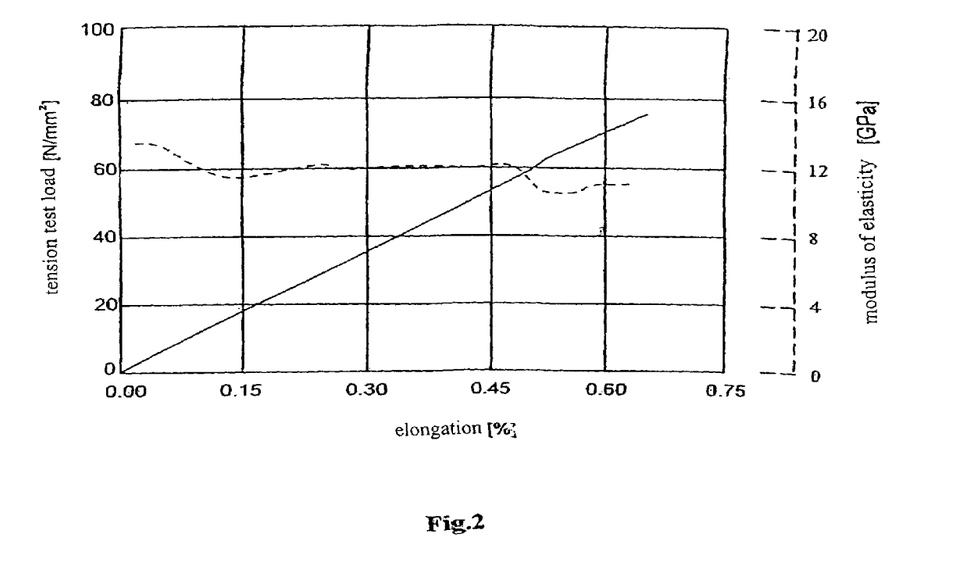

FIG. 2 shows a typical stress-strain diagram (solid line) and its derivation (dashed line), the modulus of elasticity, for timber. During the tensile test, the time, force and elongation are recorded. The evaluation software continuously calculates the tension from the force signal and the known initial cross-section.

It is advantageous to classify the greenware piece by piece and section by section after the moisture test and a machine-assisted external and internal optical inspection, for example, as follows: A=top quality; B=minor quality, R=quality showing cracks, with useability. Unusable parts are lopped out and removed from the production process. After this first production stage, the timber pieces are divided according to the above-indicated classes. This is followed by timber jointing. The parts of a respective class or quality level are assembled piece by piece into a string via a jointing technique (e.g. finger jointing). Upon reaching the selected final length, the string is divided into the desired length of the long timber—e.g. 8 m—and the long timbers thus obtained are conveyed into the space for aging the adhesive or glue, respectively, allocated to the respective quality level. This procedure is repeated for all quality levels. Then, the products of the second production stage are already provided separately in terms of quality, but still without a tension test.

After the aging period for the adhesive, the tensile test is carried out in a manner ranked according to product classes.

By way of FIGS. 3 to 7, it is explained below how to proceed in the test for tensile strength.

Figure 3A:
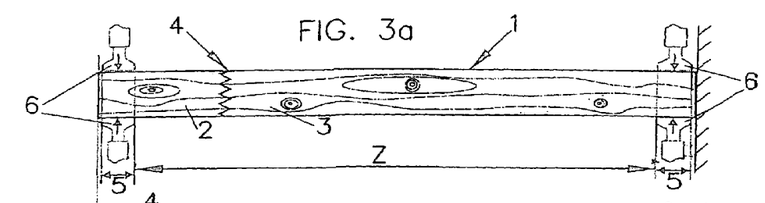
FIGS. 3 to 7 illustrate the manufacture and testing of long timbers.

A rough-planed long timber 1 formed by two pieces 2, 3 interconnected by finger jointing 4 is fastened, according to FIG. 3a, to the two ends or end regions 5, respectively, by means of clamping jaws 6 arranged in pairs and opposite each other, wherein one pair of clamping jaws 6 is preferably stationary at one end 5 of the long timber 1 and the other pair of clamping jaws 6 clamping the other end 5 of the long timber 1 is movable in the axial direction of the long timber in order to apply a tensile force.

Figure 3B:
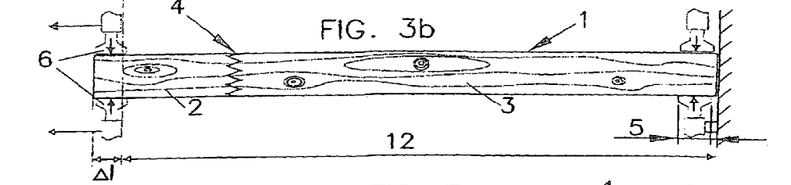
Figures 3C, 4A:
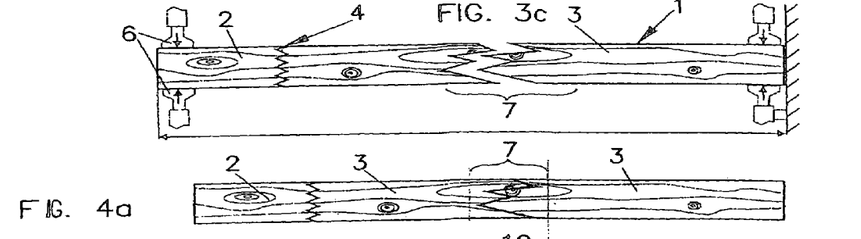
Figures 4B, 4C:
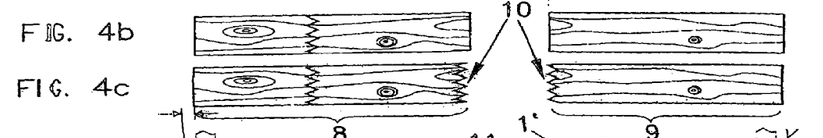

According to FIG. 3b, a first change in length Δ1 has occurred after the application of a tensile force onto the long timber 1. A further increase in the tensile force up to the final test load results in a break of the long timber 1, as illustrated in FIG. 3; the reason for this is a weak point 7 which is formed, for instance, by an internal crack etc. which remained undetected in the preliminary test. Said weak point 7 is cut out as illustrated in FIG. 4a (cf. FIG. 4b), and the two remaining pieces 8, 9 are provided with dovetails 10 at the cutting surfaces in order to be joined together again.

Figures 5A, 5B:
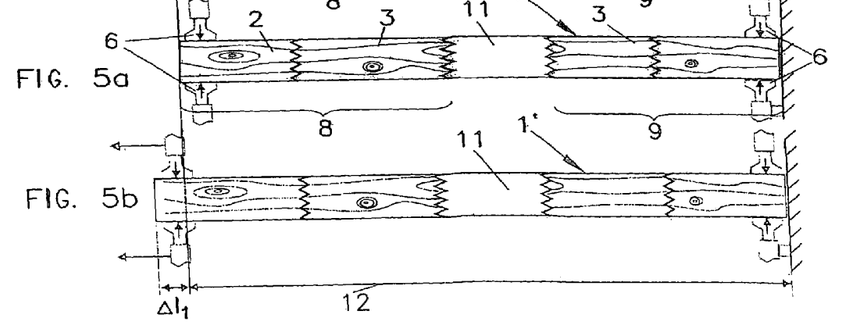

According to FIG. 5a, a further piece 11 is inserted between the two pieces 8, 9 so that the long timber 1 will again reach the original length 12 despite the weak point 7 that has been cut out. This is followed by another tensile test up to the final test load as illustrated in FIG. 5b. If the change in length $\Delta 1_1$ thereby detected is classified as admissible, the long timber 1' thus provided has passed the test.

It should be noted that the length tested at a full load is limited to the distance Z between the pairs of clamping jaws 6. The end regions 5 of the long timber 1, where it is held by the clamping jaws, are not tested under a full load, since, there, the tensile force decreases across the end regions 5.

Figure 6:
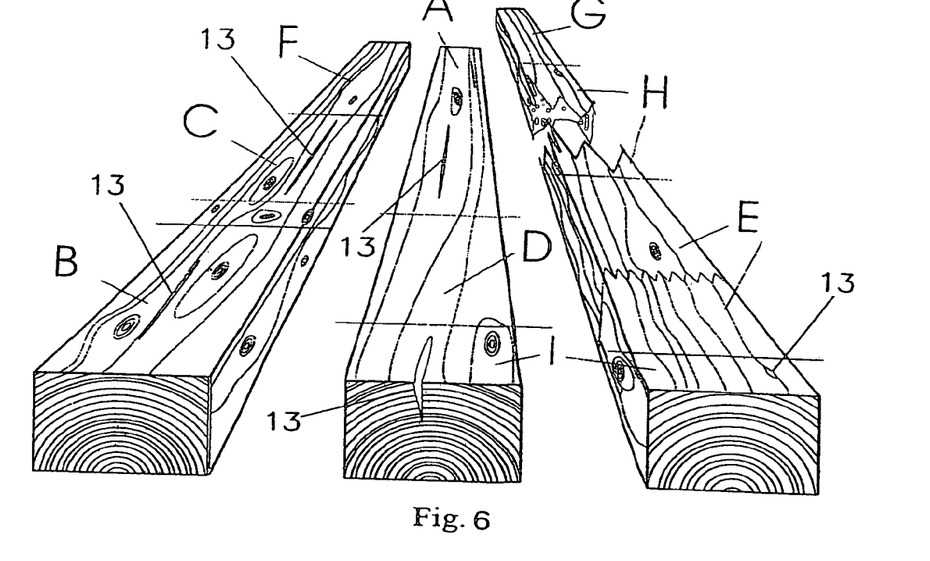
Figure 7:
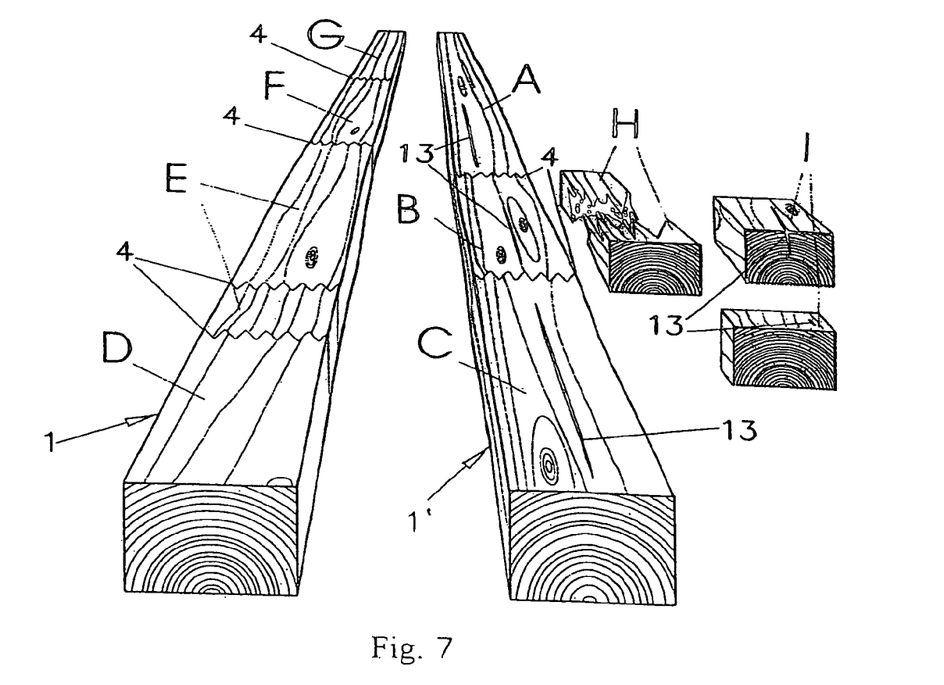

In FIG. 6, three blanks for the production of long timber are illustrated in a rough-planed state after error detection. The areas of the long timbers A, B, C and I include longitudinal cracks 13, and said areas are interconnected by finger jointings 4 in order to achieve a separate grade of long timber 1', as illustrated on the right-hand side of FIG. 7, wherein, however, the areas I produce waste material as a result of their short length. The areas D, E, F and G have no detectable defect or weak point, respectively, and are assembled into a long timber 1 by means of finger jointings 4 in order to achieve top quality. The two broken pieces H are eliminated just like the areas I. The long timbers 1 and 1' are then subjected to the tensile test according to the invention.

Figure 8:
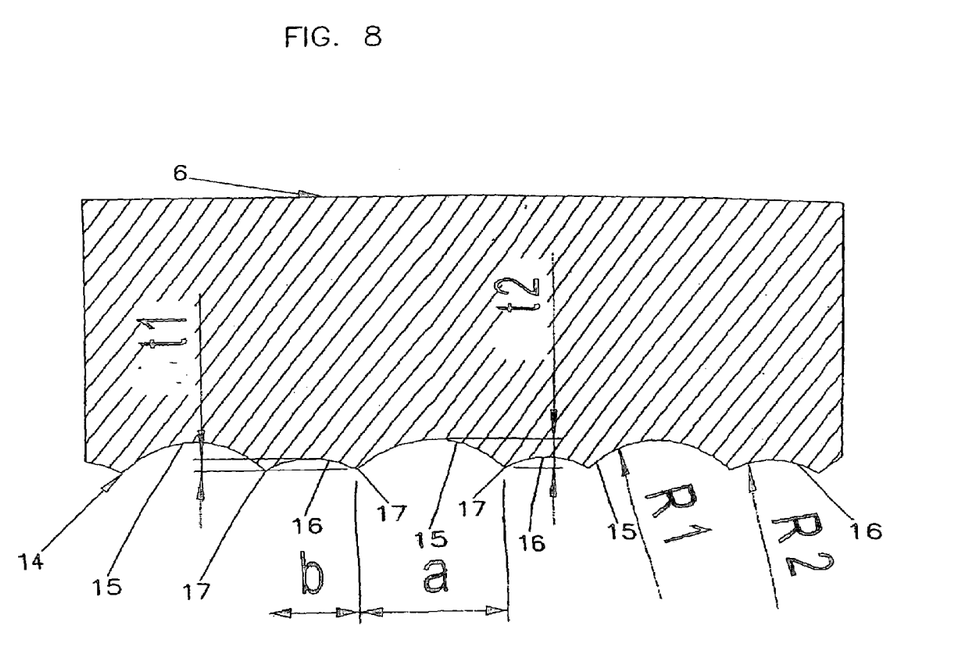
FIG. 8 shows a section through a clamping jaw.

FIG. 8 shows a clamping jaw 6 in sectional view, as it is perfectly suitable for the application of large tensile forces onto a long timber 1 in order to determine the change in length thereof Transverse grooves, i.e. grooves 15, 16 transverse to the longitudinal direction of the long timber 1 or to the direction of the tensile forces, respectively, extend across the area 14 coming into contact with the long timber 1, with the grooves 15, 16 having different depths t1 and t2. Preferably, a groove 16 of a lower depth t2 is in each case arranged beside a deeper groove 15, with the transitions 17 from groove 15 to groove 16 being designed with sharp edges.

Preferably, the cross-sections of the grooves 15, 16 are shaped in the form of a pitch circle, with the deeper groove 15 having a cross-section of a slightly larger radius R1 than groove 16 which has a lower depth t2. The ratio of the widths a, b of the grooves 15 and 16, i.e. of width b of groove 16 having a lower depth to width a of the larger groove 15, ranges between 0.3 and 0.6. The radio of radii R1 and R2 preferably ranges between 0.8 and 1.5.

Figure 9:
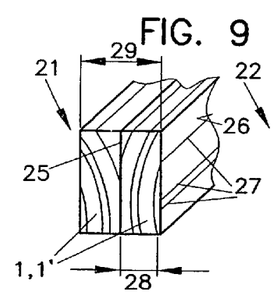
FIGS. 9 to 11 show oblique views of beams according to the invention.
Figures 10, 11:
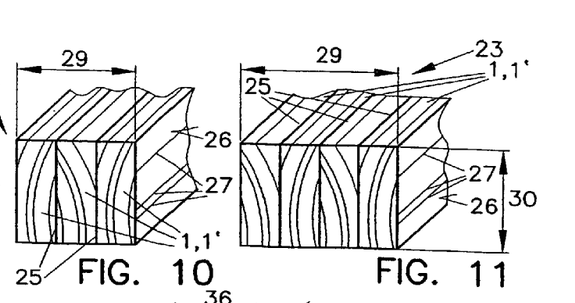

FIGS. 9 to 11 relate to so-called beams 21, 22, 23 formed from long timber 1, 1' tested according to claim 1. FIG. 9 shows a so-called duo beam 21, FIG. 10 shows a trio beam 22, and FIG. 11 shows a quattro beam 23.

The essential feature of these beams 21 to 23 is the upright glued joint 25, resulting in side surfaces 26 having a speckled texture 27. The width 28 of the long timbers 1, 1' to be glued together preferably amounts to 60 or 70 or 80 mm, resulting in beam widths 29 for a duo beam of between 120 and 160 mm. The height 30 of the long timbers 1, 1' is preferably between 200 and 300 mm. Glued joints 25 of a particularly high load-bearing capacity are produced if the vertical side faces of the long timbers 1, 1', which side faces are glued together, are processed by milling prior to gluing.

According to the invention, the beam width 29 always extends across at least two widths 28 of the long timbers 1, 1'; with a duo beam across two, with a trio beam across three, and with a quattro beam across four long timbers 1, 1'.

Figure 12:
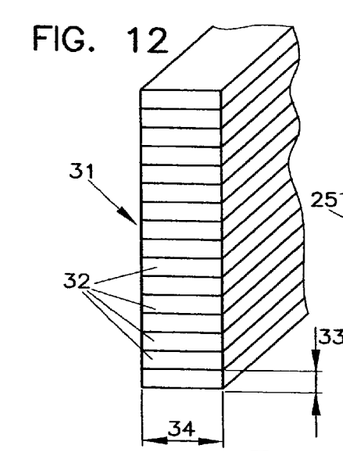
FIG. 12 illustrates a so-called "glue binder" made of glue-laminated timber.

In FIG. 12, a conventional "glue binder" 31 is illustrated which is formed from boards 32 as a glue-laminated timber. The height 33 of the individual boards usually amounts to 3 to 4 cm. The width 34 of the boards 32 usually ranges between 120 mm and 200 mm. The production of such a "glue binder" 31 is costly, and a large amount of glue or adhesive is used. The side view thereof shows all glued joints and only a plain texture with regard to the timber.

Figure 13:
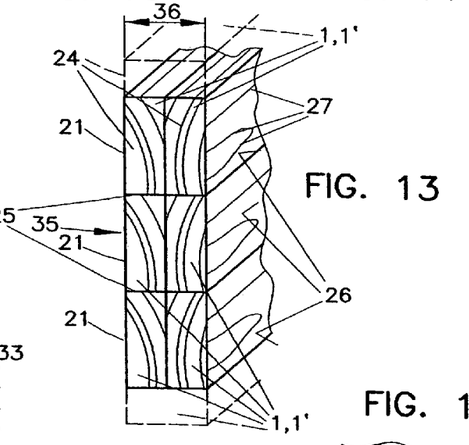
FIG. 13 shows a beam binder according to the invention, again in oblique view.

Instead of such a "glue binder", a beam binder 35 can be provided according to the invention, which, according to FIG. 13, is formed, for example, from duo beams 21 each having an upright glued joint 25, with three of such duo beams 21 placed on top of each other and glued together. The width 36 of such a beam binder likewise ranges between 120 and 200 mm but can also exceed this value, for example, if trio or quattro beams 22 or 23 are placed on top of each other and glued together.

The advantage of such a beam binder 35 over a glue binder 31 formed by boards 32 does not only consist in the optical appearance—in side view, a beautiful speckled texture 27 can be seen—but also in the load-bearing capacity, particularly since it is assembled only from long timbers 1, 1' tested individually and across the entire length. The fact that it can be formed from strong timber is another essential criterion.

In FIG. 13, it is indicated by dashed lines that long timbers 1, 1' can be glued to the bottom and/or top side of the beam binder 35 so that also the bottom and/or top side will in each case have a speckled texture and will hence be optically equivalent to a lower side of a "glue binder" 31 formed by boards 32.

Figure 14:
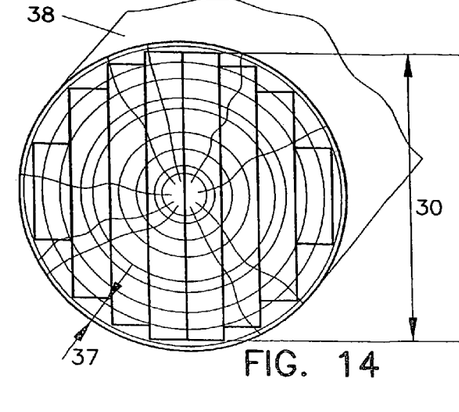
FIG. 14 shows a strong timber.

To be able to take advantage of the special strength of sapwood 37 for beams 21 to 23 and beam binders 35, respectively, strong timber 38 having diameters of more than 400 mm is split according to the cutting plan illustrated in FIG. 14. For example, long timbers 1, 1' of a height 30 of about 500 to 600 mm can thereby be produced, with the narrow edge regions 39 thereof being cut from the outer area, i.e. the sapwood area 37 of a strong timber 38.

Figure 15:
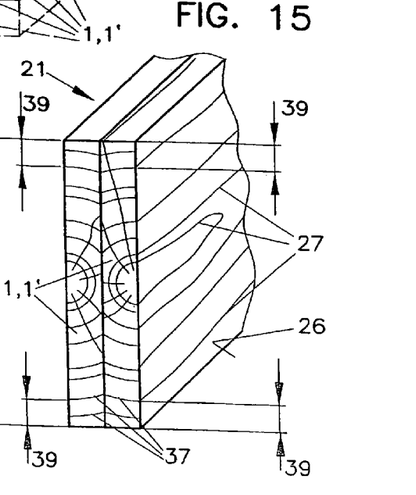
FIG. 15 again shows a beam in oblique view.

If, for example, two of such long timbers 1, 1' are glued together to form a beam 21 following a quality inspection performed according to claim 1, a beam 21 having a particularly high load-bearing capacity is produced, particularly since the tension and pressure zone of the beam is formed by sapwood 38, which, as mentioned above, has extra high strength, especially extra high tensile strength. A beam 21 of this kind, as illustrated, e.g., in FIG. 15, also has a lateral speckled texture 27 without any glued joint. A beam of such dimensions is also referred to as a tram binder.

Beams 21 as described above can be produced at particularly low cost. As can be seen in FIG. 14, the resulting timber loss is only small and, furthermore, only few production steps are necessary for the manufacture thereof.

According to the exemplary embodiment of a tension testing machine as illustrated in FIGS. 16 to 19, a test bed designed as an engine bed 41 is supported on a foundation 42. On one end, said engine bed 41 carries a first tensioning trestle 43 fixed or fixable thereto and comprising two clamping jaws 44 and 45, with one clamping jaw 44 thereof being fastened to the tensioning trestle 43 at the height of a support 46 for the long timber 1 to be tested. The second clamping jaw 45 is arranged opposite said clamping jaw 44, with said second clamping jaw being clampable against the lower clamping jaw 44 by means of a force device such as a pressure cylinder 48, whereby the long timber 1 is clamped.

Figure 18:
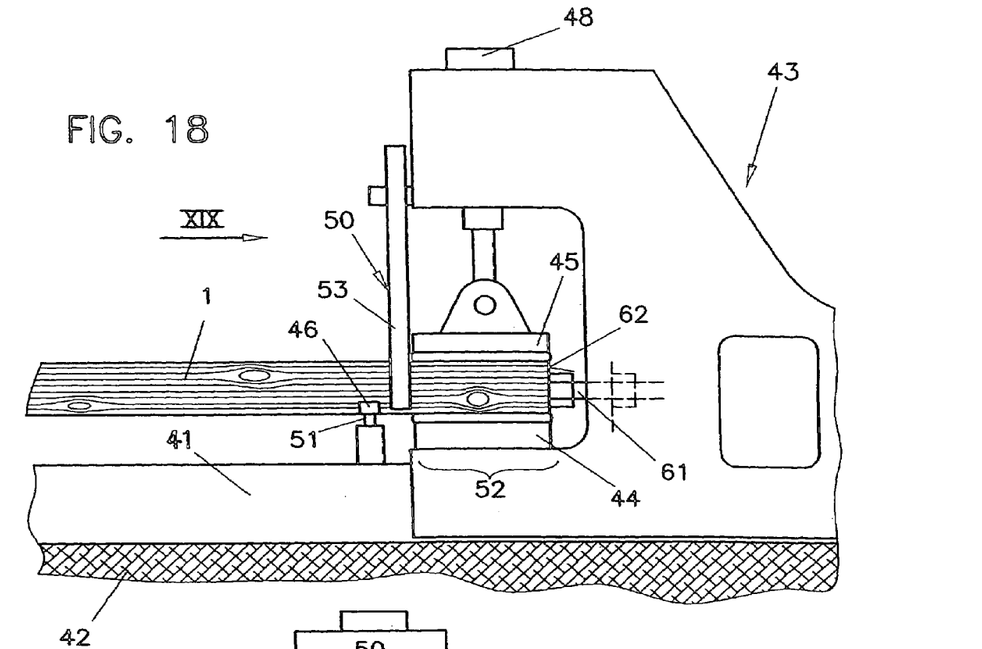
FIGS. 18 and 19 show a tensioning trestle on an enlarged scale, once in side view (FIG. 18) and once in the direction of arrow XIX of FIG. 18.

On the front side 49 of the tensioning trestle 41 oriented toward the engine bed 41, a centering means 50 for the long timber 1 to be tested is provided, which long timber is conveyable to the engine bed 41 via a cross conveyor 51 forming the support 46 and preferably formed by several conveyor chains and/or conveyor belts, respectively, arranged side by side, whereby the end region 52 of the long timber 1 ends up lying between the clamping jaws 44 and 45, as can be seen in FIG. 18.

Figure 19:
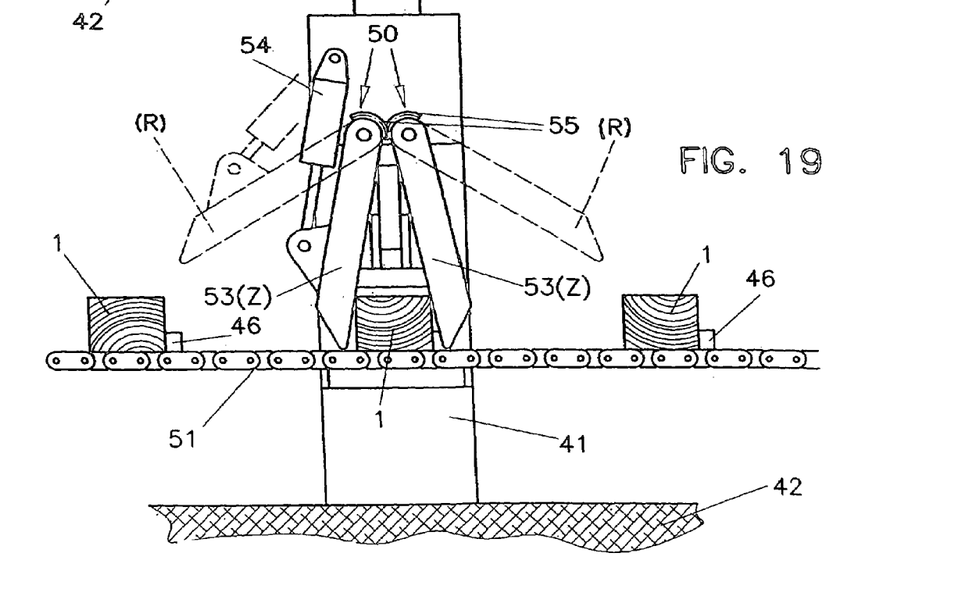

Using the centering means 50 formed by two centering arms 53 pivotably arranged on the upper part of the tensioning trestle 43, it is possible to align the position toward the tensioning trestle 43 in a precisely centric way. The centering arms 53 are pivotable synchronously by means of an adjusting device such as a pressure cylinder 54 from a rest position R disposed above the clamping jaws 44 and 45, which is illustrated in FIG. 19 by dashed lines, into a centering position Z, which centering position is illustrated in FIG. 19 by solid lines. The synchronous movement can be realized, for example, by interlocking tooth segments 55 which are connected to the centering arms 53 in a torque proof manner.

Figure 16:
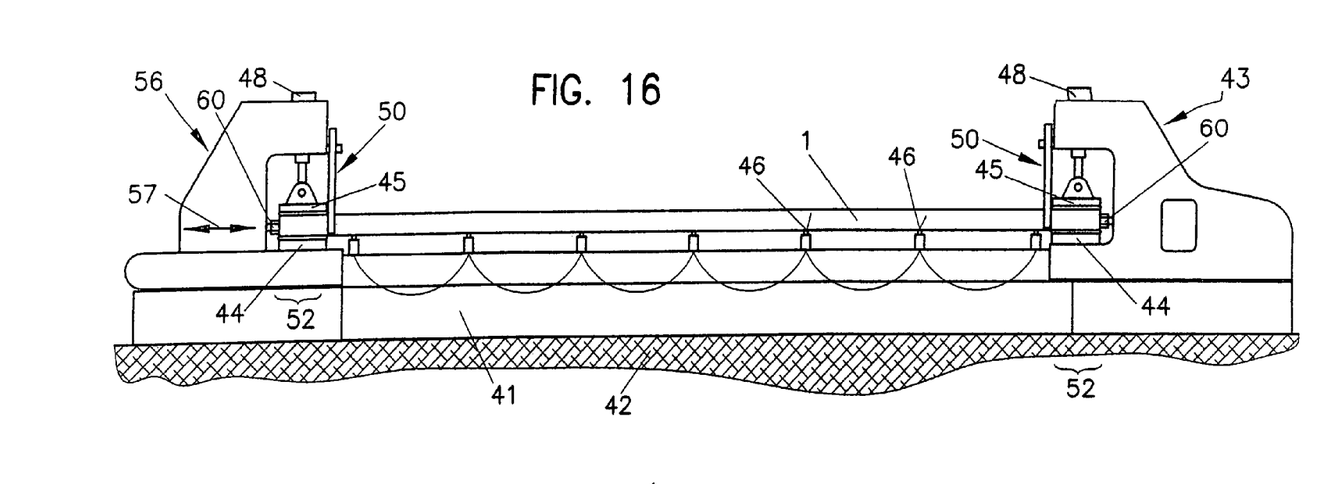
Figure 17:
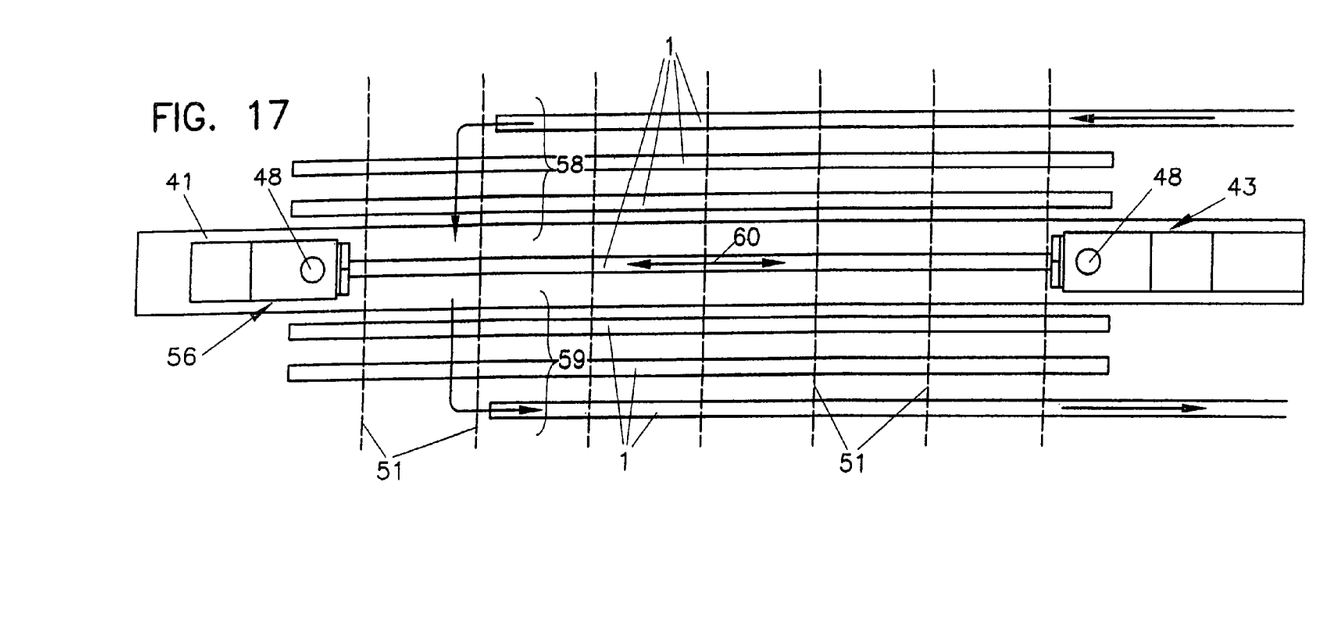
FIG. 17 a top view of a tension testing device for timber.

A second tensioning trestle 56 which has the same design as the above-described tensioning trestle 43 but is oriented in opposition thereto is provided at the other end region of the engine bed 41. Said second tensioning trestle 56 can be moved relative to the engine bed 41 (cf. double arrow 57) so that it is possible for long timbers 1 of various lengths to be gripped in each case at their end regions 52 by the clamping jaws 44, 45 of the two tensioning trestles 43 and 56.

At the side of the engine bed 41, a buffer zone 58 for long timbers 1 supplied for the test is provided, and on the opposite side thereof a storage zone 59 for long timbers 1 that have already been tested is provided, with the delivery and removal of the long timbers to and from said zones 58 and 59 in each case taking place in the longitudinal direction of the long timbers 1. After the test, an elimination flap arrangement is preferably provided where long timbers exhibiting a detected weak point are eliminated in order to be returned to the process after lopping, for example.

For applying a tensile force (illustrated by double arrow 60) to the long timber 1 after said timber has been clamped onto the two tensioning trestles 43 and 56, at least one of the tensioning trestles 43, 56 is moved away from the opposite tensioning trestle by means of a force device, which is not illustrated further in the illustrated exemplary embodiment.

In order to detect a difference in length between the long timber 1 burdened with the test load and the unstressed long timber 1, scanners 61 mounted to the tensioning trestles 43 and 56 are moved toward the front surfaces 62 of the long timber prior to the application of the test force and are pressed during the test against said front surfaces 62 with a predetermined force. A movement of the scanners 61 as a result of a change in the length of the long timber 1 is determined via suitable measuring means and transmitted to a plotting station.

In the illustrated exemplary embodiment, the engine bed 41 is designed as a box girder manufactured from sheet steel. Of course, it can also be formed by the foundation 42 itself, in which case guide rails are arranged on the foundation 42 for the movable second tensioning trestle 56, which guide rails are provided on the engine bed 41 in the illustrated exemplary embodiment.

What is claimed is:

1. A method for quality assurance of preferably finger-jointed long timber (1, 1'), produced in series and having a predetermined minimum length (12), in particular of structural solid wood, characterized in that each long timber (1, 1') finished within the length (12), preferably each long timber completely glued together, is loaded with tensile forces engaging the respective ends (5) thereof and increasing to a threshold value below the breaking load of a faultless long timber, and the change in length ($\alpha 1_1$) increasing therewith is determined in at least one section or across the entire length of the long timber (1, 1') and is used as a quality criterion for the use, or the further processing, respectively, of the long timber (1, 1').

2. A method according to claim 1, characterized in that the laser speckle method is used for determining the change in length ($\alpha 1_1$).

3. A method according to claim 1, characterized in that a method of differential length measurement is used with a direct measuring method (scaled path measurement) for determining the change in length ($\alpha 1_1$).

4. A method according to claim 1, characterized in that an indirect measuring method (e.g. resistance change in strain gauges) is used for determining the change in length ($\alpha 1_1$).

5. A method according to claim 1, characterized in that, if the long timber (1, 1') breaks, the tensile stress determined during the breakage is used for classifying the quality of the broken pieces for usage or further processing thereof.

6. A method according to claim 1, characterized in that, in case an inadmissibly high change in the length of the long timber (1) is determined at a predetermined tensile force, the long timber (1) is eliminated from the production, the weak point (7) of the long timber (1) causing the inadmissible change in length or the weak points of the long timber, respectively, is/are cut out and the remaining parts (8, 9) of the long timber that are free from weak points are assembled by finger jointing (4) into a new long timber, optionally with further long timber parts (11) being added, whereupon the newly produced long timber (1') is again subjected to the method according to claim 1.

7. A method according to claim 1, characterized in that the tensile forces are applied to the long timber (1) via clamping jaws (6) provided at the ends (5) of the long timber on two opposing sides.

8. A method according to claim 1, characterized in that finish-machining of the long timber (1, 1') such as, for example, by planing, grinding or milling is carried out after the test.

9. A method according to claim 1, characterized in that the long timbers (1, 1') are allocated to at least two different quality classes depending on the result of the length change determination.

10. A method according to claim 1, characterized in that, after a surface analysis, the raw material, being undivided and/or divided into sections, is sorted into quality classes and is subjected in each quality class as an individual long timber to a method for quality assurance according to claim 1, optionally after finger jointing.

11. A method according to claim 1, characterized in that at least two long timbers (1, 1'), which meet a quality criterion required for an application, are glued together, whereby a beam (21, 22, 23) having an upright glued joint (25) is formed.

12. A method according to claim 11, characterized in that the vertical side faces of the long timbers (1, 1'), which side faces are glued together, are processed by milling prior to gluing.

13. A method according to claim 11, characterized in that three or more long timbers (1, 1') are arranged side by side and glued together to form a beam (22, 23).

14. A method according to claim 11, characterized in that beams (21, 22, 23) which in each case have an upright glued joint (25) are placed on top of each other and glued together to form a beam binder (35).

15. A beam (21) manufactured according to claim 11 and a beam binder (35), formed of a plurality of beams (21, 22, 23) which are placed on top of one another and glued together, characterized in that the beam (21) has at least one upright glued joint (25) and the side faces forming the glued joint (25) are processed by milling and further characterized in that the beam (21) or beam binder (35) is formed from long timbers (1, 1') having a height (30) of more than 300 mm, preferably of up to 600 mm, and a width (28) of more than 50 mm, wherein long timbers (1, 1') are used the narrow edge regions (39) of which are cut from the sapwood of a strong timber.

16. A beam (21) manufactured according to claim 11 and a beam binder (35), formed of a plurality of beams (21, 22, 23) which are placed on top of one another and glued together, characterized in that the beam (21) has at least one upright glued joint (25) and the side faces forming the glued joint (25) are processed by milling and further characterized by the arrangement and gluing of at least one long timber (1, 1') at the bottom side and/or top side, which long timber extends across the entire width (29) of the beam (21) or beam binder (35), respectively, and is likewise tested according to claim 1 and exhibits a speckled texture (27) towards the bottom or the top, respectively.

17. A device for carrying out the method according to claim 1, characterized by a tension testing facility applying tensile forces to a long timber and comprising clamping jaws (6) whose sides engaging the long timber are provided with grooves (15, 16) having an arcuate, preferably circular-arc-shaped, cross-section and running transversely to the direction of loading, as well as a device detecting changes in the length of the long timber (1, 1') and a device detecting tensile forces.

18. A device according to claim 17, characterized in that adjacent grooves (15, 16) have different depths (t1, t2).

19. A device according to claim 18, characterized in that adjacent grooves (15, 16) have cross-sections of different curvatures (1/R1, 1/R2).

20. A device according to claim 18, characterized in that adjacent grooves (15, 16) have different widths (a, b).

21. A device according to claim 18, characterized in that a groove (15) having a larger depth (t1) and a larger width (a) and a less pronounced curvature (1/R1) is in each case followed by a groove (16) having a smaller depth (t2) and a smaller width (b) and a more pronounced curvature (1/R2).

22. A device according to claim 18, characterized in that the grooves (15, 16) are arranged next to each other.

23. A device for carrying out the method according to claim 1, for long timber, in particular for strong timber, characterized by a combination of the following features:
   a test bed (41), in particular an engine bed, having a length corresponding to the maximum length of the long timber (1) to be tested,
   a first tensioning trestle (43) arranged, preferably fixedly arranged, in an end region of the test bed (41),
   a second tensioning trestle (56) movable along the test bed (41) and adjustable to the length of the long timber (1) to be tested,
   clamping jaws (44, 45) provided at both tensioning trestles (43, 56) which grip and clamp a long timber (1) brought into the test position from above and from below,
   a device for the application of tensile force onto a clamped long timber (1) by means of a tensioning trestle (43, 56), as well as a device for detecting the tensile forces and detecting the changes in the length of the long timber (1) caused by the tensile forces,
   a cross conveyor (51) for conveying a long timber (1) from a buffer zone (57) for long timbers (1), which is arranged at the side of the test bed (41), to the test bed (41) and onwards to a storage zone (58) arranged opposite the buffer zone (57) and at the side of the test bed (41) and receiving the tested long timbers (1), as well as
   a centering means (50) for centering a long timber (1) brought into the test position between the clamping jaws (44, 45).

24. A device according to claim 23, characterized in that the cross conveyor (51) is formed by several conveyor chains arranged side by side.

25. A device according to claim 23, characterized in that the centering means (50) comprises two centering arms (53) which are movable, preferably pivotable, from a rest position (R) above the upper clamping jaw (45) into a centering position (Z) disposed beside the clamping jaws (44, 45).

26. A device according to claim 25, characterized in that the centering arms (53) are movable synchronously against the long timber (1), namely in each case from one side.

27. A device according to claim 23, characterized in that a scanner (60) to be applied to a front surface (61) of the long timber (1) is provided on each tensioning trestle (43, 56) for carrying out a length difference measurement.

* * * * *